United States Patent
Yoshioka et al.

(10) Patent No.: US 9,611,573 B2
(45) Date of Patent: Apr. 4, 2017

(54) NONWOVEN FABRIC AND TEST TOOL

(71) Applicant: PANASONIC INTELLECTUAL PROPERTY MANAGEMENT CO., LTD., Osaka (JP)

(72) Inventors: Yuki Yoshioka, Osaka (JP); Takayoshi Yamaguchi, Osaka (JP); Takahiro Kurokawa, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/938,469

(22) Filed: Nov. 11, 2015

(65) Prior Publication Data
US 2016/0258092 A1 Sep. 8, 2016

(30) Foreign Application Priority Data
Mar. 6, 2015 (JP) .................. 2015-045063

(51) Int. Cl.
*G01N 21/75* (2006.01)
*D04H 3/018* (2012.01)
*G01N 33/52* (2006.01)
*D04H 1/4391* (2012.01)
*D04H 1/728* (2012.01)

(52) U.S. Cl.
CPC ........... *D04H 3/018* (2013.01); *D04H 1/4391* (2013.01); *D04H 1/728* (2013.01); *G01N 33/521* (2013.01)

(58) Field of Classification Search
CPC ...... D04H 3/018; D04H 1/728; D04H 1/4391; G01N 33/54306; G01N 33/521
See application file for complete search history.

(56) References Cited

U.S. PATENT DOCUMENTS

2007/0274862 A1* 11/2007 Harttig ................ G01N 33/543
422/400

FOREIGN PATENT DOCUMENTS

JP 2013-078708 A 5/2013
WO 2014/013635 A1 1/2014

OTHER PUBLICATIONS

Fong et al, "Beaded nanofibers formed during electrospinning" Polymer 40 (1999) 4585-4592.*

* cited by examiner

*Primary Examiner* — Dennis M White
(74) *Attorney, Agent, or Firm* — Pearne & Gordon LLP

(57) ABSTRACT

A nonwoven fabric includes a fiber including a first portion and a second portion connected to the first portion. A first fiber diameter of the first portion is smaller than a reference fiber diameter. A second fiber diameter of the second portion is equal to or greater than the reference fiber diameter. The reference fiber diameter is smaller than 1 μm. A ratio of a maximum fiber diameter of the second portion to a length of a linear line connecting both end portions of the second portion is from 1/10 to 1/3.

12 Claims, 7 Drawing Sheets

NONWOVEN FABRIC AND TEST TOOL

CROSS-REFERENCES TO RELATED APPLICATION(S)

This application is based on and claims priority from Japanese Patent Application No. 2015-045063 filed on Mar. 6, 2015, the entire contents of which are incorporated herein by reference.

BACKGROUND

1. Field of the Invention

One or more embodiments of the present invention relate to a nonwoven fabric and, for example, relate to a nonwoven fabric which is used in a membrane of a test tool using immunochromatography.

2. Description of Related Art

There are strong demands of a test tool which can easily and rapidly execute an extracorporeal diagnosis with high accuracy by a non expert of a clinical test according to enhancement of home healthcare or community healthcare in recent years. For example, a dry test tool (biosensor) using an immunoassay method such as immunochromatography can quantitatively or qualitatively and extremely easily analyze a test substance in a test solution, without preparation of a reagent.

The test tool described above is generally configured with a sheet-shaped porous material (membrane) in which the test solution is moved, a base sheet which holds the sheet-shaped porous material, and a reagent carried in a part of the porous material. The test substance can be analyzed with a simple operation of applying a solution including the test substance to a predetermined location of the porous material. Such a test is required to be performed faster and more accurately.

Below-described Patent Document 1 discloses a laminated nonwoven fabric in which two types of nanofibers having different fiber diameters are laminated, as the membrane used in such a test tool. That is, a surface area of the laminated nonwoven fabric can be secured with the nonwoven fabric having a small fiber diameter, and a movement speed of the test solution is improved with the nonwoven fabric having a large fiber diameter.

Patent Document 1 is Pamphlet of International Publication No. 2014/013635, and Patent Document 2 is JP-A-2013-78708.

SUMMARY

However, in the laminated nonwoven fabric of the related art, the surface area and the movement speed of the test solution may not be sufficient. In the immunochromatography, the test solution moves in the inner part of the membrane by a capillary phenomenon, while forming an immune complex with a reagent (for example, an antibody labeled with a metal colloid and on the like). Accordingly, in order to satisfy both rapidity and high accuracy of a diagnosis, it is necessary to rapidly move the inner part of the membrane while causing the test solution to efficiently react with the reagent. In order to increase a capillary effect, sufficient voids are necessary in the membrane.

According to an aspect of one or more embodiments of the invention, there is provided a nonwoven fabric including: a fiber including a first portion and a second portion connected to the first portion, in which a first fiber diameter D1 of the first portion is smaller than a reference fiber diameter Dx, a second fiber diameter D2 of the second portion is equal to or greater than the reference fiber diameter Dx, the reference fiber diameter Dx is smaller than 1 μm, and a ratio $D2_{max}/L2$ of a maximum fiber diameter $D2_{max}$ of the second portion to a length L2 of a linear line S2 connecting both end portions of the second portion is from 1/10 to 1/3.

According to another aspect of the embodiments of the invention, there is provided a test tool which quantitatively or qualitatively detects a test substance in a test solution, the test tool including: the nonwoven fabric described above; a base sheet which is bonded to one main surface of the nonwoven fabric; and a reagent which reacts with the test substance carried in the nonwoven fabric.

According to the embodiments, it is possible to provide a nonwoven fabric which has a large surface area and a high porosity.

DETAILED DESCRIPTION

A nonwoven fabric according to the invention includes a fabric including a first portion and a second portion connected to the first portion. A first fiber diameter D1 of the first portion is smaller than Dx and a second fiber diameter D2 of the second portion is equal to or greater than the Dx. The Dx is smaller than 1 μm. A ratio $D2_{max}/L2$ of a maximum fiber diameter $D2_{max}$ of the second portion to a length L2 of a linear line S2 connecting both end portions of the second portion is from 1/10 to 1/3. Accordingly, the surface area and the porosity of the nonwoven fabric are increased.

It is preferable that the maximum fiber diameter $D2_{max}$ of the second portion is from 2 to 50 times the Dx. In addition, the Dx is preferably from 50 nm to 900 nm. Accordingly, the surface area and the porosity of the nonwoven fabric can be increased more.

The second portion preferably has a spindle shape formed such that a fiber diameter becomes smaller towards both ends. In this case, regarding the second portion, a maximum acute angle θ formed by a linear line S2 connecting both end portions of the second portion and a tangent line of an outer periphery of the second portion is preferably from 5 degrees to 45 degrees, when the nonwoven fabric is viewed from the normal direction. Accordingly, the movement speed of a test solution can be increased more.

When the nonwoven fabric is viewed from the normal direction, two or more second portions preferably exist in a square region R having one side which is 100 times the Dx. Accordingly, the porosity can be increased more.

In addition, a plurality of peak values of the second fiber diameter D2 may exist in the second portion. That is, the second portion may have one or more narrow portions having a decreased fiber diameter. Accordingly, the porosity can be increased further more.

The fiber may further include a third portion. The third portion is a portion having a fiber diameter equal to or greater than the Dx and a ratio $D3_{max}/L3$ of a maximum fiber diameter $D3_{max}$ of the third portion to a length L3 of a linear line S3 connecting both end portions of the third portion which is greater than 1/3. In this case, the number of second portions included in the region R is preferably greater than the number of third portions. Accordingly, the surface area of the nonwoven fabric can be increased more.

In addition, the test tool according to the invention is a test tool which quantitatively or qualitatively detects the test substance in the test solution, and includes the nonwoven fabric, a base sheet which is bonded to one main surface of the nonwoven fabric, and a reagent which reacts with the test substance carried in the nonwoven fabric. Accordingly, a highly accurate test can be rapidly performed.

Hereinafter, embodiments according to the invention will be described with reference to FIGS. 1 to 3.

Figure 1:
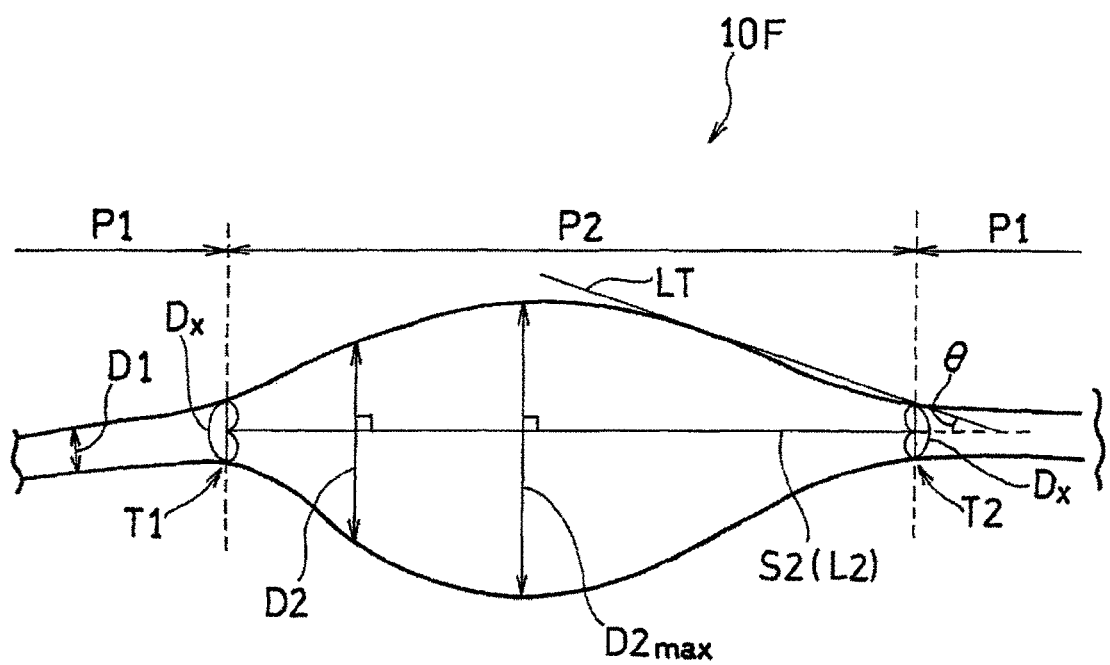
FIG. 1 is a top view schematically showing a part of a fabric when a nonwoven fabric 10 according to an embodiment of the invention is viewed from a normal direction.
Figure 2:
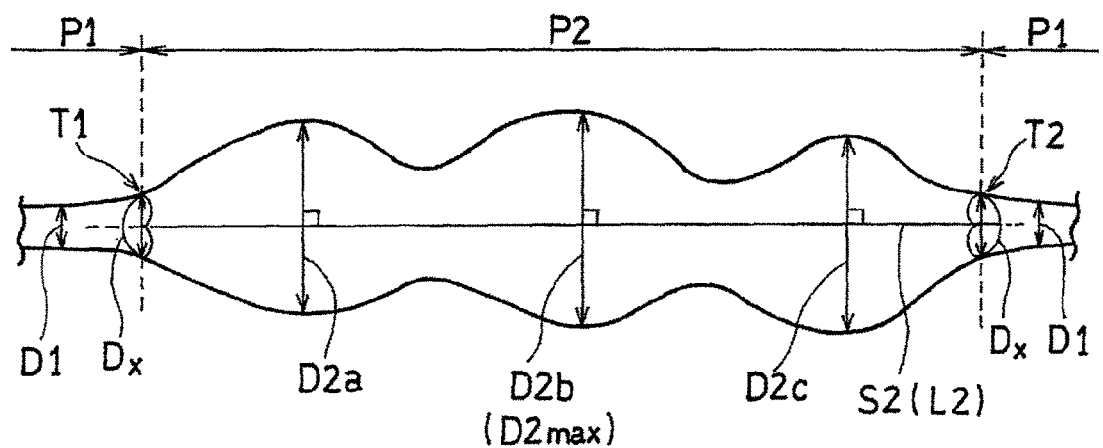
FIG. 2 is a top view schematically showing a part of a fabric when the nonwoven fabric 10 according to another embodiment of the invention is viewed from a normal direction.
Figure 3:
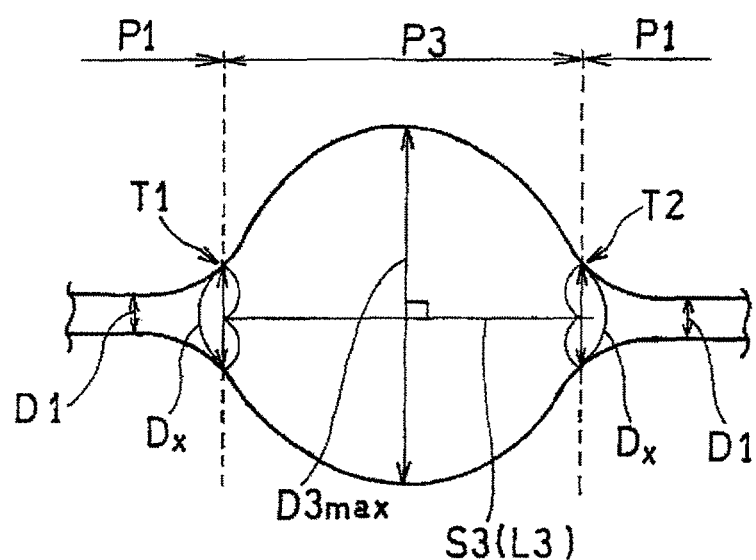
FIG. 3 is a top view schematically showing a part of a fabric when the nonwoven fabric 10 according to still another embodiment of the invention is viewed from a normal direction.

FIGS. 1 to 3 are top views schematically showing a part of a fiber 10F when each nonwoven fabric 10 according to each of different embodiments of the invention is viewed from a normal direction of the nonwoven fabric 10.

The nonwoven fabric 10 includes the fiber 10F including a first portion P1 having a fiber diameter D1 which is smaller than a fiber diameter Dx arbitrary set in a range smaller than 1 μm, a second portion P2 having a fiber diameter D2 equal to or greater than the Dx. That is, a portion having a fiber diameter less than the Dx is the first portion P1 and the other portion is the second portion P2. The Dx is preferably arbitrarily set from a range of 50 to 900 nm, and more preferably set from a range of 50 nm to 700 nm. Accordingly, the surface area of the nonwoven fabric is easily increased.

Herein, the fiber diameter is a diameter of the fiber. The diameter of the fiber is a diameter of a cross section vertical to a length direction of the fiber. When the cross section is not a circle, the maximum diameter may be assumed as the diameter. In addition, a width of the fiber in a direction vertical to the length direction, when the fiber is viewed from the normal direction of the main surface of the nonwoven fabric 10 may be assumed as the diameter of the fiber.

With an example of the latter case, a determination method of the first portion P1 and the second portion P2 will be described. For example, an electron micrograph is captured with a magnification of approximately 1000 to 8000 in the normal direction of the main surface of the nonwoven fabric 10. Next, in the captured image, an arbitrary region including a thin fiber portion and a thicker fiber portion is determined. At that time, a thick fiber portion of which the entire outer periphery can be clearly identified is set to be included in the region. A fiber successively including the thick fiber portion and the thin fiber portion in which the thin fiber portion is linear is selected from the region. A direction of the linear line of the thin fiber portion is set as the length direction of the fiber.

Next, the fiber diameter Dx as a reference is set. The Dx may be arbitrarily set in a range smaller than 1 μm, according to the purpose of the nonwoven fabric, and on the like.

When a diameter of an arbitrary 1 point of the thin fiber portion is measured and a diameter of a measurement point of the thin fiber portion is smaller than the Dx, this point is determined as the first portion P1. The measurement of the diameter is performed while moving the measurement point in a direction approaching the thick fiber portion, the first portion P1 is determined. Herein, a point where the diameter first becomes equal to or greater than the Dx is set as one end portion T1 of the second portion P2.

Here, the measurement of the diameter is performed while moving the measurement point in a direction approaching the thick fiber portion from the thin fiber portion on the opposite side by interposing the thick fiber of the same fiber, and a point where the diameter first becomes equal to or greater than the Dx is assumed as the other end portion T2 of the second portion P2. When there is no point where the diameter is smaller than the Dx while continuously performing the measurement from the end portion T2 to the end portion T1, the temporary end portion T2 is determined as the actual end portion T2. When there is a point where the diameter is smaller than the Dx while continuously performing the measurement to the end portion T1, a point where the diameter of a portion which is closest to the end portion T1 is smaller than the Dx is the actual end portion T2. A region between the end portions T1 and T2 is the second portion P2. In addition, when the diameter of an arbitrary portion of the thin fiber portion is equal to or greater than 1 μm, it can be determined that this fiber is not the fiber 10F satisfying the embodiment. In this case, this operation is performed again for other fibers. In addition, when the diameter of an arbitrary portion of the thin fiber portion is equal to or greater than the Dx, this operation may be performed again by changing a set value of the Dx.

The nonwoven fabric 10 is an aggregate in which one or more fibers 10F are randomly overlapped (or wound). The second portion P2 having a large fiber diameter exists in a part of one fiber 10F, and accordingly, when the aggregate is formed using one or more fibers 10F, the voids are easily generated between the fibers 10F. Therefore, the capillary effect is increased. Meanwhile, the first portion P1 having a small fiber diameter exists, and accordingly, the surface area of the nonwoven fabric 10 is increased. In addition, when the nonwoven fabric 10 includes two or more fibers 10F, the first portion and the second portion of each fiber 10F are determined by applying the same reference (fiber diameter Dx) to the fibers 10F in one nonwoven fabric.

Since the voids and the surface area of the nonwoven fabric 10 can be increased by only one type of the fiber 10F, without using two or more types of fibers, it is advantageous in a viewpoint of productivity. In addition, the fiber 10F preferably occupies 95% by mass or more of the entire nonwoven fabric 10. The nonwoven fabric 10 may include smaller than 5% by mass of fibers (for example, a fiber including only the first portion or the second portion) other than the fiber 10F. The fibers other than the fiber 10F are not particularly limited and can be suitably selected.

When the fiber configuring the nonwoven fabric includes only the first portion P1, that is, when the nonwoven fabric is configured with only a fiber having a fiber diameter smaller than 1 μm, the fiber is excessively dense, the voids between fibers becomes small, and the capillary effect hardly occurs. When the fiber configuring the nonwoven fabric includes only the second portion, that is, when the nonwoven fabric is configured with only a fiber having a fiber diameter equal to or greater than 1 μm, the surface area is decreased. Accordingly, when using this nonwoven fabric in the test tool using immunochromatography, the reaction between the reagent carried in the nonwoven fabric and the test solution is not sufficient and thus, the accuracy is deteriorated.

The ratio $D2_{max}/L2$ of the maximum fiber diameter $D2_{max}$ of the second portion P2 to the length L2 of the linear line S2 connecting both end portions T1 and T2 of the second portion P2 is from 1/10 to 1/3. When the maximum fiber diameter $D2_{max}$ is in this range with respect to L2, the sufficient voids can be formed between the fibers 10F. When the maximum fiber diameter $D2_{max}$ is smaller than 1/10 of L2, it is difficult to form sufficient voids between the fibers 10F. When the maximum fiber diameter $D2_{max}$ is greater than 1/3 of L2, the second portion P2 becomes a shape close to a sphere. Accordingly, the voids between the fibers 10F become excessively large and the surface area is easily decreased.

The maximum fiber diameter $D2_{max}$, the length L2, and the like may be an average value of the plurality of second portions P2. An average ratio $D2_{max}/L2$ of an average value of the maximum fiber diameters $D2_{max}$ to an average value of the lengths L2 of the plurality of second portions P2 also satisfies a range of 1/10 to 1/3. Also, regarding numerical value ranges which will be described later, numerical values as a reference may be an average value thereof. When one fiber 10F includes two or more second portions P2, the average values can be calculated by calculating and averaging the maximum fiber diameters $D2_{max}$ and the lengths L2 regarding two to five arbitrary second portions P2, for example. Alternatively, the average value may be an average of two to five arbitrary second portions P2 formed in the plurality of fibers 10F included in the region R, for example.

The maximum fiber diameter $D2_{max}$ of the second portion P2 is the largest fiber diameter in a certain second portion P2. In the same manner as described above, the fiber diameter of the second portion P2 is a diameter of a cross section vertical to the length direction of the second portion P2, or a width of the second portion P2 in a direction vertical to the length direction, when the nonwoven fabric 10 is viewed from the normal direction of the main surface thereof. In addition, the length direction of the second portion P2 can be defined as a direction of the linear line S2 connecting points respectively dividing the both end portions T1 and T2 of the second portion P2 into two.

The length L2 of the second portion P2 (linear line S2) is 3 to 10 times the maximum fiber diameter $D2_{max}$. When the second portion P2 is longer than this, a rate of the first portion P1 occupying the fiber 10F is relatively decreased and the surface area of the nonwoven fabric is decreased.

The maximum fiber diameter $D2_{max}$ of the second portion P2 is preferably from 2 to 50 times the Dx, more preferably from 2 to 20 times the Dx, and particularly preferably from 2 to 10 times the Dx. Accordingly, it is possible to increase the porosity to improve the capillary effect and it is easy to increase the surface. In the same viewpoint, the maximum fiber diameter $D2_{max}$ is preferably from 0.7 μm to 3 μm and more preferably from 0.8 μm to 2 μm.

The shape of the second portion P2 is not particularly limited. Among examples, in order to further increase the capillary effect, a spindle shape, shown in FIG. 1, in which the fiber diameter D2 becomes smaller from a portion having the maximum fiber diameter $D2_{max}$ towards the both end portions T1 and T2 of the second portion is preferable.

Regarding the second portion P2 having a spindle shape, when the nonwoven fabric 10 is viewed from the normal direction of the mains surface thereof, the maximum acute angle θ formed by the linear line S2 and a tangent line LT of an outer periphery of the second portion P2 is preferably from 5 degrees to 45 degrees, more preferably from 5 degrees to 30 degrees, and even more preferably from 5 degrees to 15 degrees. Accordingly, the capillary effect is further increased and moving speed of the fluid is easily increased.

When the nonwoven fabric 10 is viewed from the normal direction of the mains surface thereof, two or more second portions P2 preferably exist, four or more second portions more preferably exist, and seven or more second portions particularly preferably exist in the square region R having one side which is 100 times the Dx. This is because the porosity between the fibers 10F is easily increased. For the number of second portions P2, an electron micrograph is captured in the same manner as described above, and the region R is determined from the image. The number of second portions is acquired by counting the second portions where at least a part of the outer periphery is clear in the region R. The second portion, at least a part of which is included in the region R, may be counted as one portion. In this case, the second portion P2 may be formed in one arbitrary fiber 10F or may be formed in the plurality of different fibers 10F.

As shown in FIG. 2, the second portion may have a plurality of peak values of the second fiber diameter D2. That is, the second portion may include one or more narrow portions having a decreased fiber diameter. Accordingly, the porosity is easily increased, compared to a case of not including the narrow portion. In FIG. 2, the peak value of the second fiber diameter D2 is a portion including each of fiber diameters D2a, D2b, and D2c. Any one of the fiber diameters corresponds to the maximum fiber diameter $D2_{max}$. FIG. 2 shows a case where the fiber diameter D2b corresponds to the maximum fiber diameter $D2_{max}$.

The fiber may further include the third portion. As shown in FIG. 3, the third portion is a portion having the fiber diameter equal to or greater than the Dx and the ratio $D3_{max}/L3$ of the maximum fiber diameter $D3_{max}$ of the third portion to the length L3 of the linear line S3 connecting both end portions of the third portion is greater than 1/3. That is, the third portion has a shape which is closer to the sphere. When the fiber 10F includes the third portion, the number of second portions included in the region R is preferably greater than the number of the third portions, in a viewpoint of the surface area. The $D3_{max}$ can be calculated by the same method as in the case of the $D2_{max}$.

Next, the test tool of the embodiment will be described.

A test tool 20 of the embodiments is a test tool which quantitatively or qualitatively detects the test substance in the test solution, and includes the nonwoven fabric 10, the base sheet which is bonded to the main surface of the nonwoven fabric 10, and the reagent which reacts with the test substance carried in the nonwoven fabric 10.

Figure 4A:
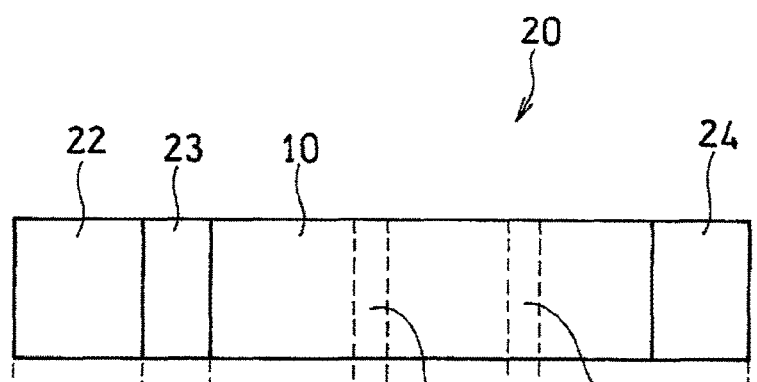
FIGS. 4A and 4B are a top view and a sectional view schematically showing a test tool according to the embodiments of the invention.
Figure 4B:
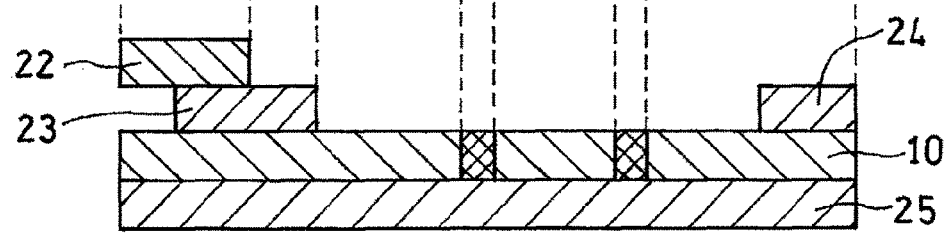

The shape of the test tool 20 is not particularly limited, but is a rectangular shape shown in FIGS. 4A and 4B, for example. A sample pad 22 for introducing the test solution including body fluid such as blood, urine, saliva, or mucous membrane swab, or a chemical component and on the like to the nonwoven fabric 10 is disposed on one short side of the rectangular test tool 20. A conjugate pad 23 is disposed between the sample pad 22 and the nonwoven fabric 10. A reagent (labeling reagent a1) specifically bonding to the test substance included in the test solution which is moved from the sample pad 22 by a penetration behavior is held in the conjugate pad 23.

The nonwoven fabric 10 is bonded to a base material 25 through the main surface thereof and moves the test solution which has moved to the conjugate pad 23, to an absorption pad 24 disposed on the other short side of the test tool 20 by the capillary effect. The nonwoven fabric 10 includes a test portion 10a which carries a solid phase antibody reagent (also referred to as an antigen-specific antibody) a2 for capturing a conjugate of the test substance and the reagent, in a line shape extending in a short side direction, and a control portion 10b which carries a solid phase antibody reagent (also referred to as a reference antigen-specific antibody) a3 for capturing the reagent which is not formed as the conjugate with the test substance, in a line shape extending in the short side direction.

When a labeling antibody m1 which is labeled with colored particles is added to the test portion 10a, the conjugate and the labeling antibody m1 form a composite and exhibit a color, and a test line appears in the test portion 10a. With the appearance of the test line, the test substance is determined to be included in the test solution. In the same manner as described above, when a labeling antibody m2 which is labeled with colored particles is added to the control portion 10b, the labeling reagent a1 and the labeling antibody m2 form a composite and exhibit a color, and a control line appears in the control portion 10b. With the appearance of the control line, it is confirmed that the test is completed without any problems.

Next, a principle of detecting the test substance in the test solution by the test tool 20 will be described in detail, using a biosensor as an example.

First, several droplets of the test solution are added to the sample pad 22 of the biosensor 20. The test solution to be added is generally body fluid collected from a living body and includes various substances. Herein, a case in which the body fluid includes Influenza A Antigen which is the test substance will be described.

The test solution added dropwise to the sample pad 22 moves to the conjugate pad 23 by the penetration behavior. The labeling reagent a1 specifically bonding to Influenza A Antigen included in the test solution is held in the conjugate pad 23, and the labeling reagent a1 and Influenza A Antigen included in the test solution generate a conjugate. In addition, anti-Influenza A Antigen labeled with gold colloid or the like is used in the labeling reagent a1.

Next, the generated conjugate moves in the inner portion of the nonwoven fabric 10 towards the test portion 10a by the capillary effect. The solid phase antibody reagent a2 for capturing a conjugate and the labeling antibody m1 are carried in the test portion 10a in a line shape. The solid phase antibody reagent a2 is, for example, anti-Influenza A Antigen which does not have labeling. A conjugate is captured by the solid phase antibody reagent a2 and the captured conjugate and the labeling antibody m1 further form a composite. Accordingly, the composite is colored and a test line appears in the test portion 10a. This test line can be easily visually checked by a tester. Since the nonwoven fabric 10 has a large surface area, sufficient reaction between the solid phase antibody reagent a2 and the test solution carried in the nonwoven fabric 10 occurs and the accuracy is improved. In addition, since the voids are formed among the fibers 10F, a penetration speed of the test solution is also improved. Therefore, the high accuracy test is rapidly performed.

Meanwhile, the labeling reagent a1 which is not formed as the conjugate with the test substance further moves in the inner portion of the nonwoven fabric 10 towards the control portion 10b by the capillary effect. The solid phase antibody reagent a3 for capturing the labeling reagent a1 and the labeling antibody m2 are carried in a line by the control portion 10b. The labeling reagent a1 is captured by the solid phase antibody reagent a3, and the captured labeling reagent a1 and the labeling antibody m2 further forms a composite. Accordingly, the composite is colored and a control line appears in the control potion 10b. This control line can also be easily visually checked by a tester.

The test solution component not captured in the test portion 10a or the control portion 10b is absorbed by the absorption pad 24. In addition, anti-Influenza A Antigen which is labeled and exists in the test portion 10a can also be determined by an optical analysis method using laser or an electrochemical analysis method, for example, in addition to the visual detection.

[Nonwoven Fabric]

The nonwoven fabric 10 disposed in the test tool 20, for example, has the same shape as that of the test tool 20, or a rectangular shape including a long side which is slightly shorter than a long side of the rectangular test tool 20 and a short side which is as long as a short side of the test tool 20.

The mass per unit area of the nonwoven fabric 10 is preferably from 5 g/m$^2$ to 50 g/m$^2$ and more preferably from 10 g/m$^2$ to 40 g/m$^2$, in order to carry the reagent. In the same viewpoint, an average thickness of the nonwoven fabric 10 is preferably from 10 µm to 200 µm. The average thickness is, for example, an average value of thicknesses of 10 arbitrary portions of the nonwoven fabric. The thickness is a distance between two main surfaces of the nonwoven fabric.

Examples of materials of the fiber 10F configuring the nonwoven fabric 10 include cellulose resins such as cellulose or nitrocellulose, a biopolymer such as polylactic acid, polyglycolic acid, collagen, polyhydroxy butyric acid, polyvinyl acetate, or polypeptide, fluorine resin such as polyvinylidene fluoride (PVDF) or a vinylidene fluoride-hexafluoropropylene copolymer, polycaprolactone, polyamide, polyimide, polyamideimide, polyacrylonitrile, polymethyl methacrylate, a acrylonitrile-methacrylate copolymer, polyvinyl chloride, a vinylidene chloride-acrylate copolymer, polyester (polyethylene terephthalate, polybutylene terephthalate, polyethylene naphthalate, poly-m-phenylene terephthalate, or poly-p-phenylene isophthalate), polyethylene, polypropylene, polystyrene, polyurethane, polyethylene oxide, polyvinyl alcohol, and polyether sulfone. These may be used alone or in combination of plurality of kinds A direction of the linear line S2 of the second portion P2 is preferably the same as a direction D in which the test solution moves from the sample pad 22 towards the absorption pad 24. This is because the movement speed of the test solution is further increased. Specifically, an angle formed by a long side of the rectangular test tool 20 and the linear line S2 is preferably smaller than 45 degrees. For example, one arbitrary second portion P2 is selected from the nonwoven fabric 10 configuring the test tool 20, and the linear line S2 is drawn. When the angle formed by the linear line S2 and the long side is smaller than 45 degrees, the direction of the liner line S2 can be assumed as the same as the direction D. Regarding the 50% or more, preferably 60% or more of second portion P2 of the second portion P2 included in the nonwoven fabric 10 configuring the test tool 20, it is preferable that the direction of the linear line S2 and the direction D are the same.

[Base Sheet]

The base material 25, for example, has the same shape as that of the nonwoven fabric 10.

The material of the base material 25 is not particularly limited, and for example, a stripe-shaped resin sheet, a paper sheet, a fabric sheet, or a glass fiber sheet can be used. As a resin configuring the resin sheet, polyolefin, polyamide, polyimide, or polyester (polyethylene terephthalate or polybutylene terephthalate) can be used. The base material 25 may have a porous structure. A thickness of the base material 25 is not particularly limited, and is preferably from 50 μm to 150 μm.

[Sample Pad]

The shape of the sample pad 22 is, for example, a rectangle including one side, a length of which in the long side direction of the nonwoven fabric 10 is from 1/15 to 1/5 of the long side of the nonwoven fabric 10, and one side, a length of which in the short side direction of the nonwoven fabric 10 is the same as the short side of the nonwoven fabric 10.

The sample pad 22 is, for example, a nonwoven fabric. The material of the nonwoven fabric is not particularly limited, and for example, paper, a glass fiber, cellulose, or a synthetic fiber is used. As the synthetic fiber, polyolefin, polyamide, polyimide, polyester (polyethylene terephthalate or polybutylene terephthalate), or polyacryl is used. Among these, the sample pad 22 is preferably a nonwoven fabric including a cellulose fiber, in a viewpoint of the absorption speed.

In the same viewpoint, the mass per unit area of the sample pad 22 is preferably from 0.1 g/cm$^3$ to 5.0 g/cm$^3$ and the thickness thereof is preferably from 50 μm to 1000 μm. In addition, a surfactant, a water-repellent agent, an antibacterial agent, a preservative, an antioxidant, or the like may be included in the sample pad 22.

[Conjugate Pad]

The shape of the conjugate pad 23 is, for example, a rectangle including one side, a length of which in the long side direction of the nonwoven fabric 10 is from 1/15 to 1/5 of the long side of the nonwoven fabric 10, and one side, a length of which in the short side direction of the nonwoven fabric 10 is equal to or smaller than the short side of the nonwoven fabric 10. Accordingly, the test solution absorbed by the conjugate pad 23 is easily penetrated through the nonwoven fabric 10 without leakage.

In the same manner as in the case of the sample pad 22, the conjugate pad 23 is also for example, a nonwoven fabric. For the material thereof, the same materials as those of the sample pad 22 can also be exemplified. In addition, a surfactant, a water-repellent agent, an antibacterial agent, a preservative, an antioxidant, or the like may also be included in the conjugate pad 23, within a range of not disturbing a holding property of the reagent.

[Absorption Pad]

The shape of the absorption pad 24 is not particularly limited and may be a shape which can collect the test solution. In addition, the configuration or the material thereof is not particularly limited, and for example, the same materials as those of the sample pad 22 can be exemplified.

[Manufacturing Method of Nonwoven Fabric]

The nonwoven fabric 10 according to the embodiments is acquired by accumulating the fiber 10F on a target (for example, the base material 25) by an electrospinning method, for example. At that time, for example, the electrospinning is performed in the temperature conditions at a normal temperature (for example, 20° C. to 30° C.) and the humidity (relative humidity) conditions of equal to or smaller than 40%, using a polar solvent as a solvent for dissolving a raw material of the fiber 10F, and accordingly, it is possible to manufacture the nonwoven fabric 10 including the fiber 10F including the first portion P1 and the second portion P2.

In the electrospinning method, the target is grounded or negatively charged a solvent (raw material solution) obtained by dissolving the raw material of the fabric 10F applied to a positive voltage is ejected from a nozzle. The solvent of the raw material solution is volatilized in a process to approach the target, the fiber-like materials (fibers 10F) of the raw materials are laminated, and the nonwoven fabric 10 is formed. Herein, the base material 25 is used as the target.

The volatilization of the solvent may be affected by the surrounding humidity. When using the polar solvent as the solvent of the raw material solution, the polar solvent has affinity to moisture in the air. Accordingly, when the electrospinning is performed in a high humidity atmosphere with approximately 60% of humidity, the solvent is easily leaked from the raw material solution and the fiber diameter is easily increased. Meanwhile, when the humidity is approximately 50%, the solvent is hardly leaked from the raw material solution, and accordingly, the fiber-like material is continued to extend, until approaching the target. Therefore, the fiber diameter can be thin.

When the humidity is further decreased (for example, equal to or smaller than 40%), the fiber-like material is further continued to extend. However, since the raw material is a polymer, the extended polymer chain is contracted to return to the original state. As a result, the extended portion and the contracted portion of the polymer chain exist in the laminated fiber-like materials (fibers 10F). For example, the extended portion is the first portion P1 and the contracted portion is the second portion P2. In addition, the method of forming the first portion P1 and the second portion P2 is not limited thereto. As other methods, a method of decreasing concentration of the raw material solution is used, for example.

Figure 5:
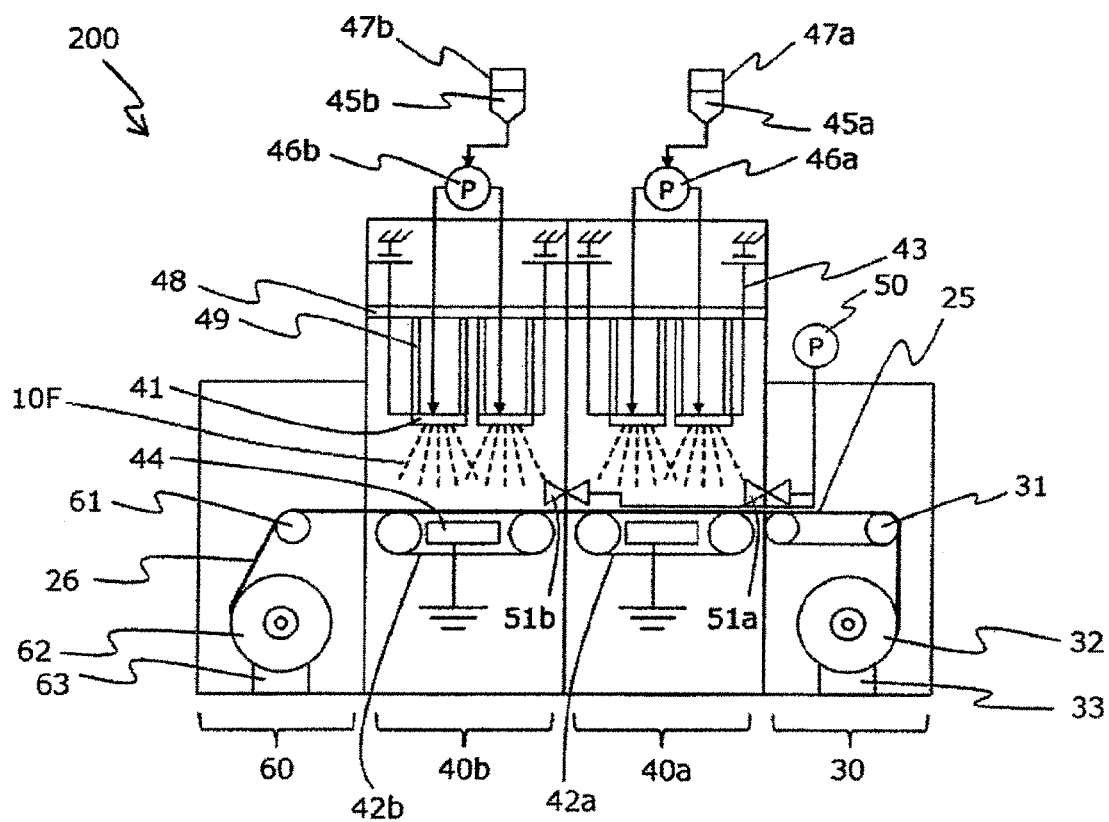
FIG. 5 is a view showing a configuration example of a part of a manufacturing system of a laminated nonwoven fabric.

The manufacturing method of the nonwoven fabric 10 using the electrospinning method will be described in detail with reference to FIG. 5. FIG. 5 is a view schematically showing a configuration of an example of a manufacturing system 200 of the nonwoven fabric 10. In addition, the method of manufacturing the nonwoven fabric 10 is not limited thereto.

First, the base material 25 is prepared. Herein, the nonwoven fabric 10 is acquired as a laminate with the base material 25. In a manufacturing system 200, the base material 25 is transported from an upstream side to a downstream side of the manufacturing line. A base sheet supply device 30 accommodating the base material 25 wound in a roll shape therein is provided on the uppermost stream side of the manufacturing system 200. The supply device 30 rotates a supply reel 32 by a motor 33 and supplies the base material 25 wound on the supply reel 32 to a first transportation conveyer 31.

The base material 25 is moved to an electrospinning unit 40 by the transportation conveyer 31. An electrospinning mechanism included by the electrospinning unit 40 includes an emitter 41 for emitting the raw material solution installed on the upper side in the device, charging means (which will be described later) for positively charging the emitted raw material solution, and a second transportation conveyer 42 which transports the base material 25 disposed so as to oppose the emitter 41 from the upstream side to the downstream side. The second transportation conveyer 42 functions as a collector portion which collects the base material 25 and the fibers 10F. In addition, the number of electrospinning units 40 is two (40a and 40b) in FIG. 5, but there is no particular limitation, and the number of electrospinning units may be one or three or more.

A plurality of injection holes (not shown) of the raw material solution are provided on the side of the emitter 41 opposing the main surface of the base material 25. A distance between the injection holes of the emitter 41 and the base material 25 depends on the scale of the manufacturing system, but may be, for example, from 100 mm to 600 mm. The emitter 41 is supported so that the longitudinal direction thereof is parallel to the main surface of the base material 25, by a second support 49 which is installed on the upper side of the electrospinning units 40a and 40b and extends downwards from a first support 48 parallel to the transportation direction of the base material 25.

The charging means is configured with a voltage application device 43 which applies a voltage to the emitter 41 and a counter electrode 44 which is installed to be parallel to the second transportation conveyer 42 (42a and 42b). The counter electrode 44 is grounded. Accordingly, it is possible to provide a potential difference (for example, 20 kV to 200 kV) according to the voltage applied by the voltage application device 43, between the emitter 41 and the counter electrode 44. In addition, the configuration of the charging means is not particularly limited. For example, the counter electrode 44 may be negatively charged. In addition, instead of providing the counter electrode 44, a belt portion of the second transportation conveyer 42 may be configured with conductors.

The emitter 41 is configured with a conductor and has an elongated shape and the inner portion thereof is hollow. The hollow portion is an accommodation portion which accommodates a raw material solution 45 (45a and 45b). The raw material solution 45 is supplied from a raw material solution tank 47 (47a and 47b) to the hollow portion of the emitter 41, by pressure of a pump 46 (46a and 46b) which is connected to the hollow portion of the emitter 41. The raw material solution 45 is emitted from the injection holes towards the main surface of the base material 25 by the pressure of the pump 46.

The emitted raw material solution causes electrostatic explosion while moving a space between the emitter 41 and the second transportation conveyer 42 in the charged state and generates the fiber-like material (fiber 10F). At that time, the humidity (relative humidity) of the inner portion of the electrospinning unit 40 is adjusted to be equal to or less than 40% and preferably equal to or less than 35%. Accordingly, the first portion P1 and the second portion P2 are formed in the generated fiber 10F.

Herein, a blast nozzle 51 (51a and 51b) connected to an air pump 50 is disposed in a space from the emitter 41 to the base material 25, gas is allowed to flow in one direction therefrom, and accordingly, the fiber 10F can be laminated on the base material 25 while aligning the fiber 10F in a certain direction. For example, when gas is allowed to flow from the upstream side to the downstream side of the second transportation conveyer 42, the fiber 10F to be laminated is easily aligned in a transportation direction (elongated direction) of the base material 25. When this alignment direction is set to be the same as the long side direction of the test tool, the direction of the linear line S2 of the second portion P2 easily becomes the same as the direction D and the movement speed of the test solution is more easily increased.

In addition, a squeegee (not shown) which comes into contact with the main surface of the base material 25 may be provided on the uppermost stream of the second transportation conveyer 42. The convexities and concavities or wrinkles on the main surface of the base material 25 before laminating nanofibers are removed and flattened by the squeegee. Accordingly, the base material 25 is easily adhered to the surface of the belt portion of the second transportation conveyer 42 and the fiber-like material is easily evenly laminated on the surface thereof The solvent included in the raw material solution of the fiber 10F may be suitably selected depending on the types of the polymer which is a raw material or the manufacturing conditions. Examples thereof include alcohols such as methanol, ethanol, 1-propanol, 2-propanol, hexafluoroisopropanol, tetraethylene glycol, triethylene glycol, or dibenzyl alcohol, cyclic ethers such as 1,3-dioxolane or 1,4-dioxane, ketones such as methylethyl ketone, methylisobutyl ketone, methyl-n-hexyl ketone, methyl-n-propyl ketone, diisopropyl ketone, diisobutyl ketone, acetone, or hexafluoroacetone, aliphatic carboxylic acid such as phenol, formic acid, methyl formate, ethyl formate, propyl formate, acetic acid, methyl acetate, ethyl acetate, or propyl acetate, or a derivative thereof, an aromatic carboxylic acid derivative such as dimethyl phthalate, diethyl phthalate, dipropyl benzoic acid methyl phthalate, ethyl benzoate, or propyl benzoate, alkyl halide such as methyl chloride, ethyl chloride, methylene chloride, chloroform, carbon tetrachloride, 1,1-dichloroethane, 1,2-dichloroethane, trichloroethane, dichloropropane, dibromoethane, dibromopropane, methyl bromide, ethyl bromide, or propyl bromide, aryl halide such as o-chlorotoluene, or p-chlorotoluene, aliphatic or aromatic hydrocarbon such as hexane, cyclohexane, cyclohexanone, cyclopentane, benzene, toluene, o-xylene, p-xylene, or m-xylene, acetonitrile, tetrahydrofuran, N,N-dimethylformamide, N,N-dimethylacetamide (DMAc), dimethyl sulfoxide, pyridine, or water. These may be used alone or in combination of plurality of kinds When forming the first portion P1 and the second portion P2 by decreasing the humidity at the time of the electrospinning, it is preferable to use the polar solvent as the solvent of the raw material solution. The polar solvent is not particularly limited, and examples thereof include alcohols, cyclic ethers, aliphatic carboxylic acid or a derivative thereof, aromatic carboxylic acid derivative, acetonitrile, tetrahydrofuran, N,N-dimethylformamide, DMAc, dimethyl sulfoxide, pyridine, or water described above. Among these, in order to easily form the second portion P2, DMAc is preferably used as the solvent.

An inorganic solid material may be added to the raw material solution.

Examples of the inorganic solid material can include oxide, carbide, nitride, boride, silicide, fluoride, or sulfide. Among these, in a viewpoint of processability, oxide is preferably used. Examples of oxide include $Al_2O_3$, $SiO_2$, $TiO_2$, $Li_2O$, $Na_2O$, $MgO$, $CaO$, $SrO$, $BaO$, $B_2O_3$, $P_2O_5$, $SnO_2$, $ZrO_2$, $K_2O$, $Cs_2O$, $ZnO$, $Sb_2O_3$, $As_2O_3$, $CeO_2$, $V_2O_5$, $Cr_2O_3$, $MnO$, $Fe_2O_3$, $CoO$, $NiO$, $Y_2O_3$, $Lu_2O_3$, $Yb_2O_3$, $HfO_2$, and $Nb_2O_5$. These may be used alone or in combination of plurality of kinds A mixing ratio of the solvent and the polymer substance of the raw material solution is different depending on the selected type of the solvent and the type of the polymer substance. The rate of the solvent in the raw material solution is, for example, from 60% by mass to 95% by mass.

A laminate 26 of the base material 25 and the nonwoven fabric 10 carried from the electrospinning unit 40 is collected in a collection device 60 disposed on the downstream side, through a transportation roller 61. A collection reel 62 which winds the transported laminate 26 is incorporated in the collection device 60. The collection reel 62 is rotatably driven by a motor 63.

[Manufacturing Method of Test Tool]

Next, the solid phase antibody reagent a2 and the solid phase antibody reagent a3 are carried in the manufactured laminate 26 in a line shape extending in the short side direction. The method of carrying each solid phase antibody reagent is not particularly limited, but for example, an aqueous solution of each solid phase antibody reagent is prepared, a proper amount of the aqueous solution is added dropwise to the nonwoven fabric 10 and dried, and accordingly, each solid phase antibody reagent can be carried. Next, the absorption pad 24, the conjugate pad 23, and the sample pad 22 are bonded to predetermined positions of the nonwoven fabric 10, and accordingly, the test tool 20 is acquired.

It is preferable to add 1% by mass to 10% by mass of alcohol (such as methanol, ethanol, or propanol) to the aqueous solution of the solid phase antibody reagent, in order to decrease polarity of the aqueous solution. In addition, a phosphoric acid buffer solution is desirably added to the aqueous solution to adjust pH to be close to 7.4.

In addition to the Influenza antibody, examples of the antibody used as each reagent include an antibody with respect to protein contained in the body fluid, and an antibody with respect to hormone contained in the body fluid. Such a antibody can be artificially produced. For example, when an antigen is sensitized to a mouse or a rabbit using protein such as albumen or hormone such as hCG or LH as an antigen, a cell for producing an antibody with respect to the antigen is acquired. A compound such as polyethylene glycol which promotes an aggregation reaction by the antigen and the antibody may coexist in a reagent holding portion, if necessary.

Hereinafter, examples of the invention will be described in detail, but the invention is not limited to the examples.

EXAMPLE 1

With the manufacturing system shown in FIG. 5, 37 g/m² of the fiber was laminated on the base sheet in the atmosphere of the temperature of 26° C. and the humidity of 40%, and a laminate in which the nonwoven fabric is laminated on the base sheet was acquired. A DMAc solution containing 50% by mass of nitrocellulose was used as the raw material solution of the fiber.

Figure 6:
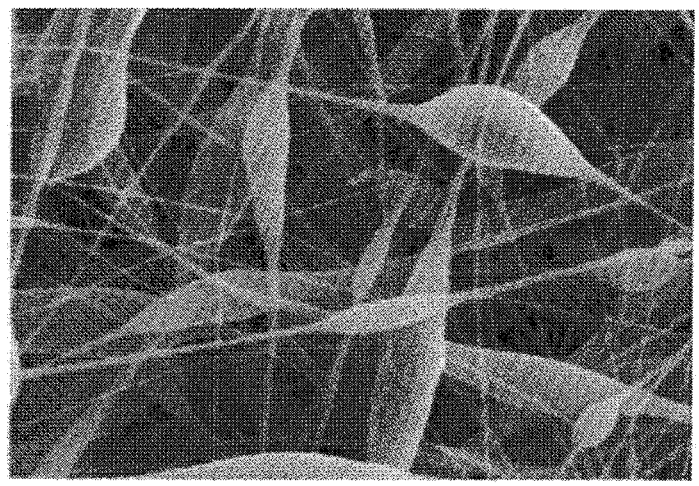
FIG. 6 is an electron micrograph of a nonwoven fabric manufactured in Example 1.

An image of the nonwoven fabric of the laminate was captured with a magnification of 5000 from the surface not opposing the base sheet. The captured image is shown in FIG. 6. The fiber diameter Dx as a reference is set as 230 nm, and one first portion P1 and one second portion P2 adjacent thereto were specified for three arbitrary fibers according to the method described above. An average value of the maximum fiber diameters $D2_{max}$ of the second portion P2 was 1.56 μm and an average value of the lengths L2 of the linear line S2 was 7.3 μm. In addition, an average value of the maximum acute angle θ formed by the linear line S2 and the tangent line of an outer periphery of the second portion P2 was 13 degrees. In the image, two or more second portions P2 were included and no third portion P3 was included in the square region R having one side which is 100 times the Dx.

COMPARATIVE EXAMPLE 1

Figure 7:
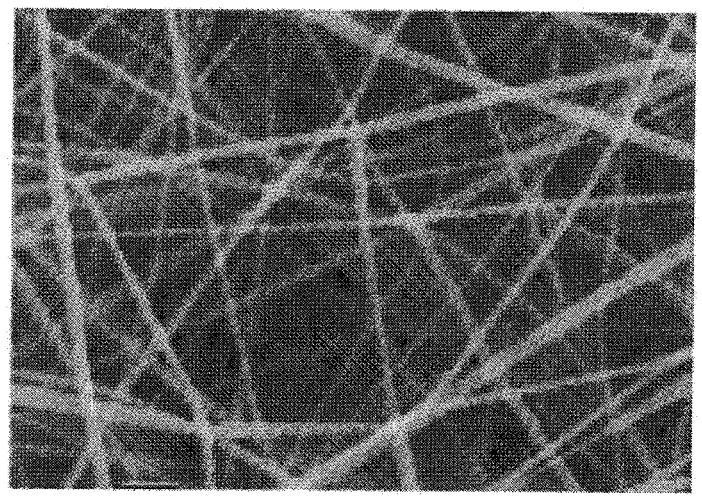
FIG. 7 is an electron micrograph of a nonwoven fabric manufactured in Comparative Example 1.

A laminate in which the nonwoven fabric is laminated on the base sheet was acquired in the same manner as in Example 1, except for setting the humidity to 58%. An image of the nonwoven fabric of the laminate was captured with a magnification of 5000 from the surface not opposing the base sheet. The captured image is shown in FIG. 7. The fiber diameter Dx as a reference was set as 480 nm. When the fiber diameters of the three arbitrary fibers of the nonwoven fabric of the acquired laminate were measured according to the method described above, a portion corresponding to the second portion P2 having the fiber diameter equal to or greater than the Dx was not observed. In addition, the average fiber diameter of the acquired fibers was 440 nm. The evaluation result is shown in Table 1.

[Evaluation Method]
Capillary Effect

The nonwoven fabric is set as a sample by cutting to have a size of width 5 mm×40 mm. 120 μL of the phosphoric acid buffer solution was added dropwise from one short side of the sample and the time the phosphoric acid buffer solution approaches the other short side was measured. The approaching time of the nonwoven fabric acquired in Example 1 was 66 seconds and the approaching time in Comparative Example 1 was 92 seconds. The approaching time is shorter in Example 1 and it was confirmed that the capillary effect is excellent.

The nonwoven fabric of the embodiments of the invention has a large surface area and an excellent capillary effect, and accordingly, can be applied to various tools (for example, a biosensor such as a tool for Influenza test or a tool for pregnancy test) for performing an extracorporeal diagnosis using immunochromatography. In addition, the nonwoven fabric of the embodiments of the invention can be applied to various tests including steps of adding a test solution including a test substance dropwise to the nonwoven fabric, moving the test solution in the nonwoven fabric, and causing a reaction with a reagent.

What is claimed is:

1. A nonwoven fabric, the nonwoven fabric comprising:
   a fiber including a first portion and a second portion connected to the first portion, wherein a first fiber diameter (D1) of the first portion is smaller than a reference fiber diameter (Dx), a second fiber diameter (D2) of the second portion is equal to or greater than the reference fiber diameter (Dx), the reference fiber diameter (Dx) is smaller than 1 .mu.m, and a ratio (D2.sub.max/L2) of a maximum fiber diameter (D2.sub.max) of the second portion to a length (L2) of a linear line (S2) connecting both end portions of the second portion is from 1/10 to 1/3, wherein the maximum fiber diameter (D2.sub.max) is from 2 to 50 times the reference fiber diameter (Dx).

2. The nonwoven fabric according to claim 1, wherein the reference fiber diameter (Dx) is from 50 nm to 900 nm.

3. The nonwoven fabric according to claim 1, wherein the second portion has a spindle shape formed such that the second fiber diameter (D2) becomes smaller towards the both ends.

4. The nonwoven fabric according to claim 3, wherein a maximum acute angle (.theta.2) formed by the linear line (S2) and a tangent line of an outer periphery of the second portion is from 5 degrees to 45 degrees, when the nonwoven fabric is viewed from a normal direction of the nonwoven fabric.

5. The nonwoven fabric according to claim 1, wherein two or more second portions exist in a square region (R) having one side which is 100 times the reference fiber diameter (Dx), when the nonwoven fabric is viewed from a normal direction of the nonwoven fabric.

6. The nonwoven fabric according to a claim 1, wherein the second portion has a plurality of peak values of the second fiber diameter (D2).

7. The nonwoven fabric according to claim 1, wherein the maximum fiber diameter ($D2_{max}$) is between 0.7 μm and 3 μm.

8. A test tool which quantitatively or qualitatively detects a test substance in a test solution, the test tool comprising:

the nonwoven fabric according to claim 1;

a base sheet which is bonded to a first main surface of the nonwoven fabric; and a reagent which reacts with the test substance carried in the nonwoven fabric.

9. The test tool according to claim 8, further comprising:

a sample pad provided on or above a second main surface of the nonwoven fabric, said sample pad containing test solution, and an absorption pad provided on the second main surface of the nonwoven fabric, which absorbs the test solution coming through the nonwoven fabric, wherein a direction of a linear line connecting both end portions of the second portion is the same as a direction in which the test solution moves from the sample pad towards the absorption pad.

10. The test tool according to claim 9, wherein 50% or more of all the linear lines of all the second portions included in the nonwoven fabric is the same as the direction in which the test solution moves from the sample pad towards the absorption pad.

11. A nonwoven fabric, the nonwoven fabric comprising:

a fiber including a first portion and a second portion connected to the first portion, wherein a first fiber diameter (D1) of the first portion is smaller than a reference fiber diameter (Dx), a second fiber diameter (D2) of the second portion is equal to or greater than the reference fiber diameter (Dx), the reference fiber diameter (Dx) is smaller than 1 .mu.m, and a ratio (D2.sub.max/L2) of a maximum fiber diameter (D2.sub.max) of the second portion to a length (L2) of a linear line (S2) connecting both end portions of the second portion is from 1/10 to 1/3, wherein the fiber further includes a third portion, a third fiber diameter (D3) of the third portion is equal to or greater than the reference fiber diameter (Dx), a ratio (D3.sub.max/L3) of a maximum fiber diameter (D3.sub.max) of the third portion to a length (L3) of a linear line (S3) connecting both end portions of the third portion is greater than 1/3, and the number of second portions included in a square region (R) having one side which is 100 times the reference fiber diameter (Dx) is greater than the number of third portions included in the square region (R), when the nonwoven fabric is viewed from a normal direction of the nonwoven fabric.

12. A nonwoven fabric, the nonwoven fabric comprising:

a first fiber including a first portion and a second portion connected to the first portion; and a second fiber including a third portion, wherein a first fiber diameter (D1) of the first portion is smaller than a reference fiber diameter (Dx), a second fiber diameter (D2) of the second portion is equal to or greater than the reference fiber diameter (Dx), the reference fiber diameter (Dx) is smaller than 1 .mu.m, and a ratio (D2.sub.max/L2) of a maximum fiber diameter (D2.sub.max) of the second portion to a length (L2) of a linear line (S2) connecting both end portions of the second portion is from 1/10 to 1/3, wherein a third fiber diameter (D3) of the third portion is equal to or greater than the reference fiber diameter (Dx), a ratio (D3.sub.max/L3) of a maximum fiber diameter (D3.sub.max) of the third portion to a length (L3) of a linear line (S3) connecting both end portions of the third portion is greater than 1/3, and the number of second portions included in a square region (R) having one side which is 100 times the reference fiber diameter (Dx) is greater than the number of third portions included in the square region (R), when the nonwoven fabric is viewed from a normal direction of the nonwoven fabric.

\* \* \* \* \*